(12) United States Patent
Shimizu et al.

(10) Patent No.: US 9,114,091 B2
(45) Date of Patent: Aug. 25, 2015

(54) SUSTAINED RELEASE SOLID DOSAGE PREPARATIONS

(71) Applicant: SHIMIZU CHEMICAL CORPORATION, Hiroshima (JP)

(72) Inventors: Hideki Shimizu, Hiroshima (JP); Hisao Shimizu, Hiroshima (JP); Ryusuke Shimizu, Hiroshima (JP)

(73) Assignee: SHIMIZU CHEMICAL CORPORATION, Hiroshima (JP)

( * ) Notice: Subject to any disclaimer, the term of this patent is extended or adjusted under 35 U.S.C. 154(b) by 0 days.

(21) Appl. No.: 13/935,969

(22) Filed: Jul. 5, 2013

(65) Prior Publication Data
US 2015/0010621 A1 Jan. 8, 2015

(51) Int. Cl.
*A61K 47/26* (2006.01)
*A61K 9/48* (2006.01)

(52) U.S. Cl.
CPC .............. *A61K 9/4866* (2013.01); *A61K 47/26* (2013.01)

(58) Field of Classification Search
None
See application file for complete search history.

(56) References Cited

U.S. PATENT DOCUMENTS

| 5,462,761 A | * | 10/1995 | McGinley et al. ............ 426/573 |
| 5,486,364 A | | 1/1996 | King et al. |
| 2006/0134785 A1 | * | 6/2006 | Fernandez et al. ............ 435/375 |
| 2010/0203078 A1 | * | 8/2010 | Gokaraju et al. ........ 424/195.18 |

FOREIGN PATENT DOCUMENTS

| JP | 4446126 | 4/2010 |
| JP | 2013-103922 | 5/2013 |

OTHER PUBLICATIONS

"Mesh to Micron Conversion Chart," available at <http://www.showmegold.-org/news/Mesh.htm>, as accessed Mar. 29, 2014.*
Khadka, P., et al., "Pharmaceutical particle technologies: An approach to improve drug solubility, dissolution and bioavailability," Asian Journal of Pharmaceutical Sciences 9: 304-316 (2014).*

* cited by examiner

*Primary Examiner* — David J Blanchard
*Assistant Examiner* — Daniel F Coughlin
(74) *Attorney, Agent, or Firm* — Greenblum & Bernstein, P.L.C.

(57) ABSTRACT

A sustained release solid dosage preparation is provided comprising an active ingredient admixed with an excipient. At least part of the excipient consists of glucomannan microparticles having an average particle size less than 50 μm. The glucomannan microparticles forms, when absorbing water, a hydrogel matrix for the active ingredient capable releasing the active ingredient almost entirely up about 6 hours.

7 Claims, 2 Drawing Sheets

US 9,114,091 B2

SUSTAINED RELEASE SOLID DOSAGE PREPARATIONS

FIELD OF THE INVENTION

This invention relates to a sustained release solid dosage preparation containing glucomannan as a sustained release excipient. The invention is applicable not only to pharmaceutical preparations but also to other preparations such as cosmetic and pesticidal preparations.

BACKGROUND ART

Sustained release solid dosage forms are conventionally produced by coating active ingredients with a water-insoluble polymer and formulating the coated active ingredients into final dosage forms together with various excipients. As such the conventional sustained release formulations rely on a mechanism in which dissolution of active ingredients in the digestive juice is controlled by the coating film of water-insoluble polymers.

U.S. Pat. No. 5,486,364 to King et al. discloses sustained release pharmaceutical tablets based on another mechanism. The sustained release tablets are produced by direct compression of dry powders of readily available konjac glucomannan alone or mixtures thereof with xanthan gum admixed with active ingredients. Examples of the readily available konjac glucomannan include clarified konjac glumomannan, cryogenetically ground konjac glucomannan and plasticized konjac glucomannan.

The dissolution properties of sustained release tablets produced in Examples are given in the specification in terms of cumulative percentage of theophiline which was released into deionized water (pH=7) during 6 hour elapsed time. The cumulative percentage varies from 14% to 74% depending upon the particular type of konjac glucomannan.

It is known that most of drugs are absorbed from the small intestine when administered orally and that the sum of the gastric emptying time and the small intestine transit time of tablets in adult human is about 6 hours or less. Because of this, a portion of the active ingredient which was not released from the solid dosage forms in the digestive tract up to the end of small intestine transit time will be excreted to outside the body and will not be available for the intended therapeutic purposes. A need exists, thereof, for a sustained release solid dosage preparation having enhanced bioavailability.

SUMMARY OF THE INVENTION

The above and other needs are met by the present invention. According to the present invention, there is provided a sustained release solid dosage preparation comprising an active ingredient and glucomannan microparticles having an average particle size less than 50 μm admixed with said active ingredient. When administered orally, the sustained release solid dosage preparation according to present invention forms a hydrogel and essentially entire portion of the active ingredient is released from the hydrogel up to about 6 hours.

DESCRIPTION OF THE PREFERRED EMBODIMENTS

Figure 1:
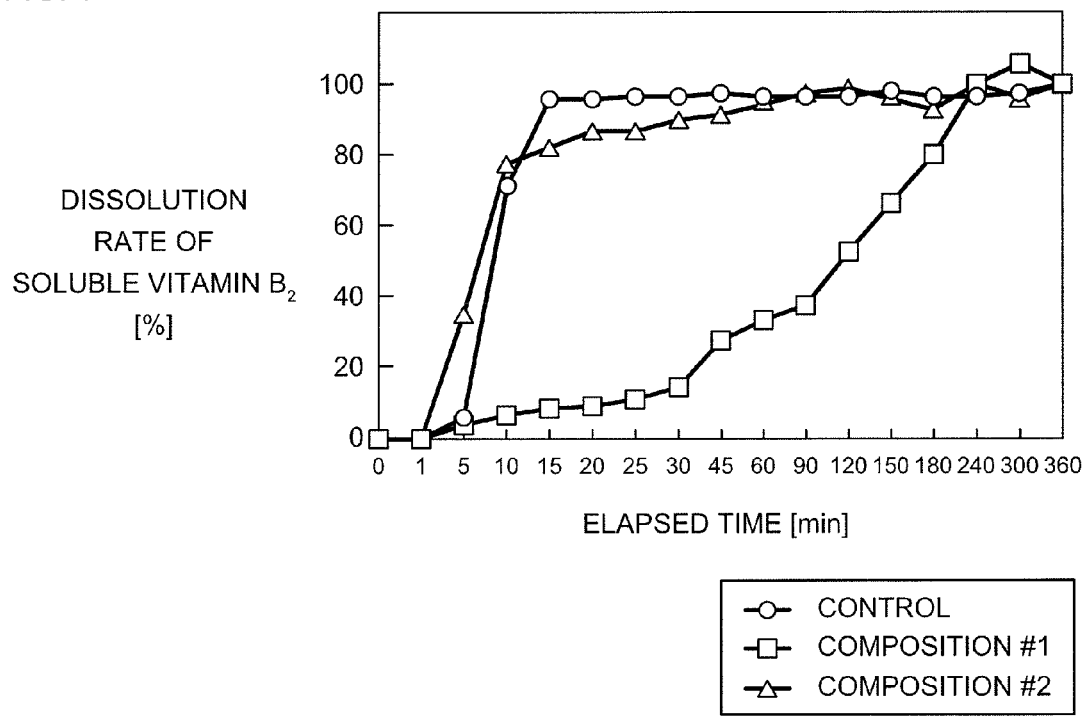
FIG. 1 shows the result of dissolution test of the sustained release solid dosage preparation of Example 1, wherein the curves Glucomannan 50 and Glucomannan 100 respectively represent percent dissolution with time of the active ingredient from Composition #1 and Composition #2.

The sustained release solid dosage preparation according to the present invention typically takes the form of tablets, powders or capsules but the invention finds use in sustained release of active ingredients from topical formulations, pesticidal and cosmetic formulations in the form of hydrogels or pastes.

The present invention utilizes rapidly soluble glucomannan microparticles having an average particle size less than 50 μm as a sustained release excipient of the solid dosage preparations. The rapidly soluble glucomannan microparticles are produced, for example, by the process disclosed in Japanese patent No. 4,446,126 assigned to the assignee of the present application. Briefly, the process comprises suspending refined konjac flour in aqueous ethanol having an ethanol concentration greater than 70% for a period of time, grinding the suspended particle, for example, by stirring the suspension using a high speed stirring device to grind the suspended konjac flour particles into finer particles, separating konjac flour particles so treated from the suspension, and drying the separated solids.

The above process takes advantages of properties of crude or refined konjac flour which is otherwise not easily grindable but becomes susceptible to grinding when reducing their water content by the diffusion into aqueous ethanol having an ethanol concentration greater than 70%.

The ground konjac glucomannan microparticles produced by the above process have the smallest particles size among known konjac glucomannan flour and generally have an average particle size less than 50 μm, for example, about 25 μm. Since the smaller in the average particle size the greater in the specific surface area, the length of time required for dissolution or swelling in water is shortened proportionally. Therefore, when an active ingredient is admixed with the glucomannan microparticles and administered orally, a hydrogel containing the active ingredient is formed in the stomach and essentially the entire portion of the active ingredient is released up to the end of the small intestine transit time, namely within about 6 hours.

The dissolution time of the active ingredient from the sustained release solid dosage preparation according to the present invention may be controlled by blending sugar alcohols, saccharides, polysaccharide or gums such as mannitol, lactose, crystalline cellulose or guar gum with the glucomannan microparticles. Thus the dissolution time may be adjusted at about 6 hours by the addition of the above substances when the dissolution time is too long in cases where the excipient consists soley of the glucomannan microparticle.

Another advantage of the glucomannan microparticles produced by the process disclosed in Japanese patent No. 4,446,126 is that they are almost free of impurities. Refined konjac glucomannan is produced by grinding dried slices of the tuber of a plant Amorphophallus konjac, and subjecting ground particles to air elutriation to remove impurities such as starch and fibrous substances. However, the refined konjac glucomannan flour still contains many impurities such as trimethylamine and sulfites and has a unique irritating smell. These impurities have been removed almost completely and the glucomannan content is increased in the glucomannan microparticles produced by the above process.

It will be appreciated that the present invention is applicable to any active ingredient desired to be formulated into sustained release solid dosage forms. Typically the active ingredient is a pharmaceutically active component to be administered orally but the invention is also applicable to an active ingredient of topical pharmaceutical preparations, cosmetic and pesticidal preparations in cases where sustained release of the active ingredient is desired.

Solid dosage forms are typically capsule preparations filled with a mixture of the glucomannan microparticles and the active ingredient, and tablets prepared by direct compression molding of the above mixture further containing a conventional lubricant such as magnesium stearate or fatty acid sucrose ester.

EXAMPLES

The following examples are offered to further illustrate the present invention without intending to limit thereto. In these examples, water-soluble vitamin $B_2$ (riboflavin 5'-phosphate) is used as a model active ingredient. "Glucomannan 50" and "Glucomannan 100" used therein are glucomannan flour having an average particle size of about 25 μm and 100 μm, available from Shimizu Chemical Corporation under the names of Rheolex™ One and Rheolex™ RS, respectively.

The particle size distribution of refined conjac glucomannan fluor, Glucomannnan 100 and Glucomannnan 50 are as follows.

| Refined konjac glucomannan flour | |
|---|---|
| >30 mesh | 0% |
| >42 mesh | 0.3% |
| >60 mesh | 39.17% |
| >80 mesh | 38.43% |
| >100 mesh | 7% |
| <100 mesh | 9.1% |

| Glucomannan 100 | |
|---|---|
| >100 mesh | 0% |
| >120 mesh | 11.8% |
| >140 mesh | 14.8% |
| >170 mesh | 27.9% |
| >200 mesh | 18.6% |
| <200 mesh | 26.9% |

| Glucomannan 50 | |
|---|---|
| >200 mesh | 0% |
| <200 mesh | 100% |

Example 1

Using mixtures of dextrin, glucomannan and water-soluble vitamin $B_2$, dissolution tests of vitamin $B_2$ were conducted.
1. Materials
    Control: 0.1 g of vitamin $B_2$+20 g of dextrin
    Composition #1: Control+10 g of Glucomannan 50
    Composition #2: Control+10 g of Glucomannan 100
    Control and compositions #1 and #2 were each encapsulated in capsule #0 according to the Japanese Pharmacopeia.

2. Test Method
    To a 500 ml beaker containing 400 ml of distilled water kept at 37° C. in a water bath were added 4 capsules filled with each test composition while stirring with a magnetic stirrer rotating at about 500 rpm. A 10 ml aliquot of vitamin $B_2$ solution was taken in a brown glass bottle at elapsed times of 1, 5, 10, 15, 20, 25, 30, 45, 60, 90, 120, 150, 180, 240 and 360 minutes and the absorbance of water-soluble vitamin $B_2$ was measured by a spectrophotometer at 450 nm. The dissolution quantity of the soluble vitamin $B_2$ was determined using a working curve (Y=0.3308x+0.00007) and percent dissolution is calculated therefrom.

3. Results
    The results obtained are shown in the graph of FIG. 1. As seen, the dissolution curve of Composition #2 containing Glucomannan 100 is almost same as the dissolution curve of control and almost all soluble vitamin $B_2$ was dissolved up to about 45 minutes demonstrating no sustained release effect. In contrast, the dissolution rate of soluble vitamin $B_2$ from Composition #1 increases proportionally with elapsed time demonstrating a sustained release effect.

Example 2

A dissolution test similar to the dissolution test in Example 1 was carried out for binary mixtures of water-soluble vitamin $B_2$ and glucomannan.

1. Materials
    Control: same as the control in Example 1 Composition #3: 0.1 g of vitamin $B_2$+10 g of glucomannan 50
    Composition #4: 0.1 g of vitamin $B_2$+10 g of glucomannan 100
    Control and Compositions #3 and #4 were each encapsulated in capsule #0 according to the Japanese Pharmacopeia.

2. Test Method
    Same as Example 1.

Figure 2:
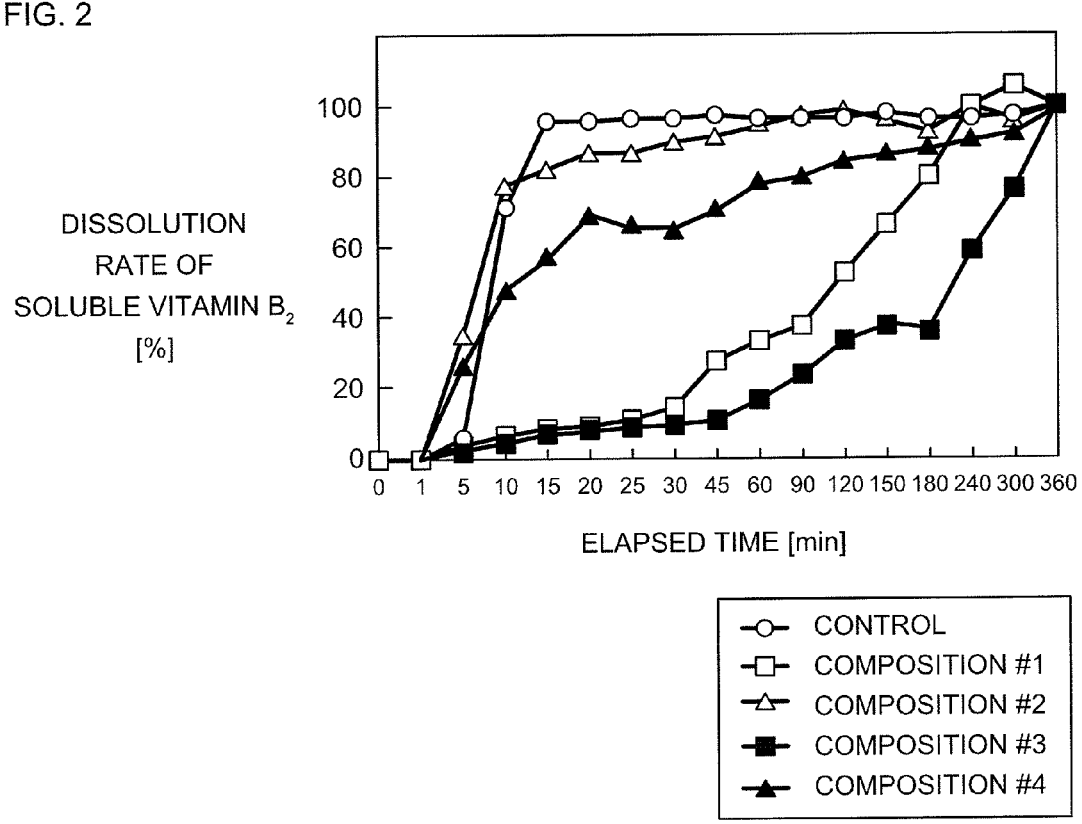
FIG. 2 shows the result of dissolution test of the sustained release solid dosage preparation of Example 2, wherein the curves Glucomannan 50 and Glucomannan 100 respectively represent percent dissolution with time of the active ingredient from Composition #3 and Composition #4.

3. Results
    The results obtained are shown in the graph of FIG. 2 in conjunction of the results of Example 1. As seen, when the composition is a binary mixture of the active ingredient and glucomannan, the dissolution percentage with time generally tends to be decreased compared with that of the corresponding ternary mixture of vitamin $B_2$, glucomannan and dextrin. However, composition #3 containing glucomannan 50 exhibited about 40% dissolution up to 180 minutes and the reminder of about 60% of vitamin $B_2$ was dissolved out up to 360 minutes demonstrating a high suspended release effect. Comparable effect is not seen in Composition #4 containing Glucomannan 100.

Example 3

Dissolution tests were carried out according to the disintegration test method in the general test method section of the Japanese Pharmacopeia, 16th edition.

1. Materials

| | |
|---|---|
| Control: Vitamin $B_2$ | 0.4% |
| Crystalline cellulose | 99.6% |
| Composition #5: Vitamin $B_2$ | 0.4% |
| Glucomannan 50 | 5% |
| Crystallin cellulose | 94.6% |
| Composition #6: Vitamin $B_2$ | 0.4% |
| Glucomannan 50 | 10% |
| Crystallin cellulose | 89.6% |

300 mg of control, Composition #5 and #6 were each encapsulated in capsule #0 according to the Japanese Pharmacopeia.

2. Test Method

The disintegration test for rapid release formulations defined in the general test method section of the Japanese Pharmacopeia, 16th edition is used in distilled water kept at 37±2° C.

3. Results

The control exhibited almost 100% dissolution at the elapsed time of 15 minutes while Composition #5 and #6 both exhibited 20 to 36% dissolution even at the elapsed time 360 minutes (6 hours). These results suggest that a sustained release solid dosage preparation having a sustained release effect over about 6 hours may be designed by adjusting the proportion of Glucomannan 50.

Example 4

| Sustained release tablets | |
|---|---|
| Glucomannan 50 | 5.0% |
| Crystalline cellulose | 93.6% |
| Vitamin $B_2$ | 0.4% |
| Sucrose fatty acid ester | 1.0% |

Except sucrose fatty acid ester, the above materials were uniformly blended to obtain a premix and then sucrose fatty acid ester was blended with the premix. The resulting dry powder was compressed into tablets each weighing 300 mg by the conventional direct compression method at two different levels of compression pressure to obtain tablets having different hardness. Disintegration time was measured for tablets having two different hardness values according to the disintegration test method in the general test method section of the Japanese Pharmacopeia, 16$^{th}$ edition.

For comparison, two control tablets having comparable hardness values were produced by dispensing with Glucomannan 50 and increasing the proportion of crystalline cellulose to 98.6%. The disintegration time of control tablets was also determined by the same method. The results are shown in Table 1 below.

TABLE 1

| Tablet | Tablet Hardness *[1] | Disintegration Time *[2] |
|---|---|---|
| Control A (glucomannan free) | 5.1 kg | <1 min. |
| Control B (glucomannan free) | 12.7 kg | 14 min. 48 sec. *[3] |
| Example 4A | 4.9 kg | 3 hrs. 55 min. *[3] |
| Example 4B | 13.2 kg | >420 min. *[3] |

*[1] Determined by Kiya Hardness meter. Mean Value of 10 tablets
*[2] Japanese Pharmacopeia, General test method, Disintegration test method, the time at which the tablet is finally disintegrated.
*[3] Mean value (n = 6) of the time at which tall Tablets have been disintegrated.

We claim:

1. A sustained release solid dosage preparation comprising an active ingredient admixed with one or more excipients, wherein at least one excipient consists of glucomannan microparticles having an average particle size of from about 25 μm to less than 50 μm which forms, when absorbing water in the digestive tract, a hydrogel matrix for the active ingredient capable of releasing the active ingredient almost entirely up to about 6 hours.

2. The sustained release solid dosage preparation according to claim 1, wherein said glucomannan microparticles pass through 200 mesh screen entirely.

3. The sustained release solid dosage preparation according to claim 1, wherein said glucomannan microparticles are produced from crude or refined konjac glucomannan flour by subjecting the flour to the wet grinding process after decreasing the moisture content by suspending in an aqueous ethanol having an ethanol concentration greater than 70% to allow diffusion of water into the aqueous ethanol.

4. The sustained release solid dosage preparation according to claim 1 further comprising an auxiliary excipient selected from the group consisting of a sugar alcohol, a saccharide, a polysaccharide, and gum.

5. The sustained release solid dosage preparation according to claim 1, wherein the mixture of said active ingredient and said excipient is encapsulated in a hard capsule.

6. The sustained release solid dosage preparation according to claim 1, wherein the mixture of said active ingredient and said excipient is directly compressed into tablets with addition of a lubricant to the mixture.

7. The sustained release solid dosage preparation according to claim 1, wherein said active ingredient is a pharmaceutically active component.

* * * * *